United States Patent
Iglesias

(10) Patent No.: US 10,470,862 B2
(45) Date of Patent: Nov. 12, 2019

(54) TREATMENT OF PELVIC ORGAN PROLAPSE

(71) Applicant: Remendium Labs LLC, Baton Rouge, LA (US)

(72) Inventor: Ramon Jose Iglesias, DeLeon Springs, FL (US)

(73) Assignee: Remendium Labs LLC, Baton Rouge, LA (US)

(*) Notice: Subject to any disclaimer, the term of this patent is extended or adjusted under 35 U.S.C. 154(b) by 0 days.

(21) Appl. No.: 14/374,314

(22) PCT Filed: Jan. 30, 2013

(86) PCT No.: PCT/US2013/023806
§ 371 (c)(1),
(2) Date: Jul. 24, 2014

(87) PCT Pub. No.: WO2013/116310
PCT Pub. Date: Aug. 8, 2013

(65) Prior Publication Data
US 2015/0032030 A1    Jan. 29, 2015

Related U.S. Application Data

(60) Provisional application No. 61/592,092, filed on Jan. 30, 2012.

(51) Int. Cl.
*A61F 2/00* (2006.01)
*A61B 5/103* (2006.01)
(Continued)

(52) U.S. Cl.
CPC .......... *A61F 2/0045* (2013.01); *A61B 5/103* (2013.01); *A61B 5/227* (2013.01); *A61B 5/4337* (2013.01); *A61B 5/4848* (2013.01)

(58) Field of Classification Search
None
See application file for complete search history.

(56) References Cited

U.S. PATENT DOCUMENTS 2,830,582 A    5/1987  Ljung
4,669,478 A    6/1987  Robertson
(Continued)

FOREIGN PATENT DOCUMENTS

CA    2625428 A1    7/2007
DE    103 45 282 B3    4/2005
(Continued)

OTHER PUBLICATIONS

Glazer, Howard et al., "Pelvic Floor Muscle Biofeedback in the Treatment of Urinary Incontinence: A Literature Review", Sep. 2006, Applied Psychophysiology and Biofeedback, Vo. 31, No. 3, pp. 187-201.*

(Continued)

*Primary Examiner* — Matthew Kremer
(74) *Attorney, Agent, or Firm* — Clark & Elbing LLP

(57) ABSTRACT

A method and device for the diagnosis and treatment of pelvic floor prolapse is provided. The diagnosis and treatment may involve the use of a multiple sensor-enabled device for vaginal insertion capable of providing real-time data regarding the patient's physiology, the position and movement of the urethra, and the muscular strength of the patient's vagina and pelvic floor. The methods and devices of the invention may also be useful to addressing other medical issues, including urinary incontinence, sexual health, and fecal incontinence, as well as facilitate patient home wellness activities.

10 Claims, 1 Drawing Sheet

(51) Int. Cl.
*A61B 5/22* (2006.01)
*A61B 5/00* (2006.01)

(56) References Cited

U.S. PATENT DOCUMENTS

| | | | |
|---|---|---|---|
| 5,328,077 A | 7/1994 | Lou | |
| 5,406,961 A | 4/1995 | Artal | |
| 5,562,717 A | 10/1996 | Tippey | |
| 5,603,685 A * | 2/1997 | Tutrone, Jr. | A61F 2/005 |
| | | | 128/836 |
| 5,674,238 A | 10/1997 | Sample | |
| 5,924,984 A | 7/1999 | Rao | |
| 6,021,781 A | 2/2000 | Thompson | |
| 6,039,701 A | 3/2000 | Sliwa et al. | |
| 6,086,549 A | 7/2000 | Neese | |
| 6,264,582 B1 | 7/2001 | Remes | |
| 6,511,427 B1 | 1/2003 | Sliwa, Jr. et al. | |
| 6,672,996 B2 | 1/2004 | Ross et al. | |
| 6,679,854 B2 | 1/2004 | Honda et al. | |
| 6,816,744 B2 | 11/2004 | Garfield et al. | |
| 7,577,476 B2 | 8/2009 | Hochman et al. | |
| 7,608,037 B2 | 10/2009 | Levy | |
| 7,628,744 B2 | 12/2009 | Hoffman et al. | |
| 7,645,220 B2 | 1/2010 | Hoffman et al. | |
| 7,837,682 B2 | 11/2010 | Ostrovsky et al. | |
| 7,955,241 B2 | 6/2011 | Hoffman et al. | |
| 7,957,794 B2 | 6/2011 | Hochman et al. | |
| 8,147,429 B2 | 4/2012 | Mittal et al. | |
| 8,360,954 B2 | 1/2013 | Kim | |
| 8,623,004 B2 | 1/2014 | Johnson et al. | |
| 8,728,140 B2 | 5/2014 | Feemster et al. | |
| 8,751,204 B2 | 5/2014 | Webster et al. | |
| 8,805,472 B2 | 8/2014 | Iglesias | |
| 8,914,111 B2 | 12/2014 | Haessler et al. | |
| 8,983,627 B2 | 3/2015 | Pelger et al. | |
| 9,155,885 B2 | 10/2015 | Wei et al. | |
| 9,248,285 B2 | 2/2016 | Haessler | |
| 9,381,351 B2 | 7/2016 | Haessler | |
| 9,656,067 B2 | 5/2017 | Pelger et al. | |
| 2001/0047132 A1 * | 11/2001 | Johnson | A61B 5/055 |
| | | | 600/410 |
| 2002/0111586 A1 | 8/2002 | Mosel et al. | |
| 2003/0028180 A1 | 2/2003 | Franco | |
| 2004/0236223 A1 | 11/2004 | Barnes et al. | |
| 2004/0260207 A1 * | 12/2004 | Eini | A61B 5/1076 |
| | | | 600/587 |
| 2005/0148447 A1 * | 7/2005 | Nady | A63B 23/20 |
| | | | 482/121 |
| 2006/0036188 A1 | 2/2006 | Hoffman et al. | |
| 2006/0074289 A1 | 4/2006 | Adler et al. | |
| 2006/0084848 A1 | 4/2006 | Mitchnick | |
| 2007/0066880 A1 | 3/2007 | Lee et al. | |
| 2007/0232882 A1 | 10/2007 | Glossop et al. | |
| 2007/0255090 A1 | 11/2007 | Addington et al. | |
| 2007/0270686 A1 | 11/2007 | Ritter et al. | |
| 2008/0077053 A1 * | 3/2008 | Epstein | A61B 5/0053 |
| | | | 600/591 |
| 2008/0139876 A1 | 6/2008 | Kim | |
| 2008/0149109 A1 * | 6/2008 | Ziv | A61F 2/005 |
| | | | 128/834 |
| 2008/0154131 A1 | 6/2008 | Lee et al. | |
| 2008/0171950 A1 | 7/2008 | Franco | |
| 2009/0149740 A1 | 6/2009 | Hoheisel | |
| 2009/0270963 A1 | 10/2009 | Pelger et al. | |
| 2009/0306509 A1 | 12/2009 | Pedersen et al. | |
| 2010/0174218 A1 * | 7/2010 | Shim | A61B 5/1107 |
| | | | 601/84 |
| 2010/0249576 A1 * | 9/2010 | Askarinya | A61B 5/06 |
| | | | 600/424 |
| 2010/0262049 A1 | 10/2010 | Novak et al. | |
| 2011/0054357 A1 | 3/2011 | Egorov et al. | |
| 2011/0077500 A1 * | 3/2011 | Shakiba | A61B 1/303 |
| | | | 600/409 |
| 2011/0190580 A1 | 8/2011 | Bennett et al. | |
| 2011/0196263 A1 | 8/2011 | Egorov et al. | |
| 2012/0016258 A1 | 1/2012 | Webster et al. | |
| 2012/0265049 A1 | 10/2012 | Iglesias | |
| 2013/0053627 A1 * | 2/2013 | Bercovich | A61F 2/005 |
| | | | 600/31 |
| 2013/0144191 A1 | 6/2013 | Egorov et al. | |
| 2013/0184567 A1 | 7/2013 | Xie et al. | |
| 2013/0192606 A1 * | 8/2013 | Ziv | A61B 17/43 |
| | | | 128/836 |
| 2013/0237771 A1 | 9/2013 | Runkewitz et al. | |
| 2013/0324380 A1 | 12/2013 | Horsley | |
| 2014/0066813 A1 | 3/2014 | Daly et al. | |
| 2014/0073879 A1 | 3/2014 | Cantor et al. | |
| 2014/0088471 A1 | 3/2014 | Leivseth et al. | |
| 2014/0155225 A1 | 6/2014 | Sedie | |
| 2014/0213927 A1 | 7/2014 | Webster et al. | |
| 2014/0296705 A1 | 10/2014 | Iglesias | |
| 2014/0309550 A1 | 10/2014 | Iglesias | |
| 2015/0032030 A1 | 1/2015 | Iglesias | |
| 2015/0112230 A1 | 4/2015 | Iglesias | |
| 2015/0112231 A1 | 4/2015 | Iglesias | |
| 2015/0133832 A1 | 5/2015 | Courtion et al. | |
| 2015/0196802 A1 | 7/2015 | Siegel | |
| 2015/0282763 A1 | 10/2015 | Rosenshein | |
| 2016/0008664 A1 | 1/2016 | Siegel | |
| 2016/0074276 A1 | 3/2016 | Scheuring et al. | |
| 2016/0346610 A1 | 12/2016 | Iglesias et al. | |
| 2017/0281072 A1 | 10/2017 | Iglesias | |
| 2017/0281299 A1 | 10/2017 | Iglesias | |

FOREIGN PATENT DOCUMENTS

| | | |
|---|---|---|
| EP | 2 689 724 A1 | 1/2014 |
| GB | 2492754 A | 1/2013 |
| JP | 2011-183167 | 9/2011 |
| WO | WO 96/05768 | 2/1996 |
| WO | WO-00/09013 A1 | 2/2000 |
| WO | WO 0009013 A1 | 2/2000 |
| WO | WO-0023030 A1 | 4/2000 |
| WO | WO-2006/107930 A2 | 10/2006 |
| WO | WO 2006107930 A2 | 10/2006 |
| WO | WO-2010/131252 A2 | 11/2010 |
| WO | WO 2010131252 A2 | 11/2010 |
| WO | 2011050252 A1 | 4/2011 |
| WO | WO-2011/050252 A1 | 4/2011 |
| WO | WO 2011121591 A2 | 10/2011 |
| WO | WO2011159906 | 12/2011 |
| WO | WO 2012079127 A1 | 6/2012 |
| WO | WO 2012138232 A1 | 10/2012 |
| WO | WO 2013082006 A1 | 6/2013 |
| WO | WO 2013116310 A1 | 8/2013 |
| WO | WO 2015103629 A1 | 7/2015 |
| WO | WO 2016026914 A2 | 2/2016 |
| WO | WO 2016042310 A1 | 3/2016 |
| WO | WO2016067023 A1 | 5/2016 |

OTHER PUBLICATIONS

Summons to attend oral proceedings pursuant to Rule 115(1) EPC, issued on Aug. 3, 2017 by the European Patent Office related to the European Patent Application No. 13743383.5.
Rosenbaum, Talli Y. et al., "The Role of Pelvic Floor Physical Therapy in the Treatment of Pelvic and Genital Pain-Related Sexual Dysfunction", 2008, J. Sex Med, 5: pp. 513-523.
Extended European Search Report for European Patent Application No. 17203166.8, dated Jul. 31, 2018 (10 pages).
Parekh et al., "The role of pelvic floor exercises on post-prostatectomy incontinence," J Urol. 170(1):130-33 (2003) (Abstract Only).
First Examination Report for Australian Patent Application No. 2018200715, dated Jun. 26, 2018 (4 pages).
Second Examination Report for Canadian Patent Application No. 2,862,928, dated Nov. 20, 2018 (5 pages).
International Search Report and Written Opinion for International Application No. PCT/US18/57811, dated Jan. 29, 2019 (18 pages).
International Preliminary Report on Patentability for International Application No. PCT/US2017/044444, dated Feb. 7, 2019 (14 pages).

(56) References Cited

OTHER PUBLICATIONS

Moen et al., "Pelvic floor muscle function in women presenting with pelvic floor disorders," Int Urogynecol J Pelvic Floor Dysfunct. 20(7):843-6 (2009).
Kandadai et al., "Correct Performance of Pelvic Muscle Exercises in Women Reporting Prior Knowledge," Female Pelvic Med Reconstr Surg. 21(3):135-40 (2015).
Rosenblatt et al., "Interactive Pelvic Floor Muscle Training for Female Urinary Incontinence," Renovia, Inc., retrieved Apr. 30, 2019 from <https://renoviainc.com/wp-content/uploads/2018/04/REN005.01-White-Paper-12Apr18-FINAL.pdf> (2018) (6 pages).

\* cited by examiner

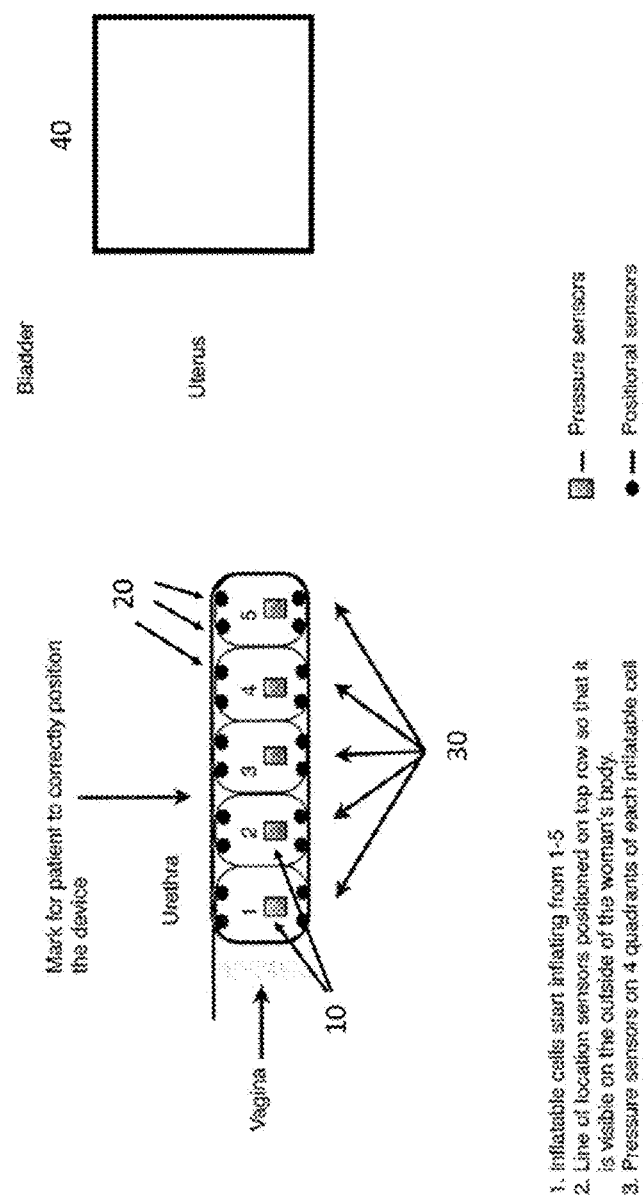

TREATMENT OF PELVIC ORGAN PROLAPSE

BACKGROUND OF THE INVENTION

The present invention relates to the diagnosis and treatment of pelvic organ prolapse and related conditions. The diagnosis and treatment may involve the use of a multiple sensor-enabled device for vaginal insertion capable of providing real-time data regarding the patient's physiology, the position and movement of the urethra, and the muscular strength of the patient's vagina and pelvic floor.

Pelvic organ prolapse (POP) generally relates to a condition where the muscles and ligaments supporting a woman's pelvic organs weaken thereby causing the pelvic organs to slip out of place (prolapse). There are different types of POP, including vaginal vault prolapse, bladder prolapse, rectal prolapse, uterine prolapse, and small bowel prolapse. Some women develop vaginal prolapse, usually after menopause, childbirth or a hysterectomy.

In certain cases, POP occurs due to the damage of the tissues that support the intra-abdominal contents causing the contents of the abdominal cavity to spill through the weakest support points and extrude through the vaginal walls. This weakness can be at the bladder area, the uterine area or the rectal/enterocele area. The condition can worsen over time, and the patient may need corrective surgery.

Information regarding the anatomical areas of weakness suspected as contributing to the condition as well as the primary area of weakness can facilitate appropriate corrective surgery at an early stage and in a targeted fashion to repair the herniated abdominal contents through the pelvic floor area. In addition, specially designed patches, for example, could be used to prevent further prolapse.

Presently, there is no available test that can accurately diagnose POP by localizing and evaluating the herniated areas suspected of giving rise to a patient's POP. The types of diagnostic tests commonly relied upon today include the cotton swab test (where the health care provider inserts a small, cotton-tipped applicator lubricated with anesthetic gel into the patient's urethra, the patient is asked to strain, and the applicator may indicate a loss of support to the urethra); the bladder function test (to measure the ability of the patient's bladder to store and empty urine, which might aid the health care provider to determine the most appropriate type of surgery for bladder or urethral prolapse); pelvic floor strength tests (where the health care provider relies upon personal experience to approximate the strength of the patient's pelvic floor and sphincter muscles, and possibly, the strength of muscles and ligaments that support the patient's vaginal walls, uterus, rectum, urethra and bladder); and imaging tests (which include magnetic resonance imaging (MRI) to obtain a three-dimensional image of the pelvis; ultrasound to visualize the patient's kidneys, bladder or the muscles around the patient's anus; cystoscopy to evaluate symptoms of urinary urgency, frequency, bladder pain or blood in the urine by insertion of a thin tube with a light and camera on the tip (cytoscope) into the patient's urethra to view the urethra and bladder. None of these techniques, however, alone or collectively, can provide the positional and pressure data to yield as detailed and accurate POP diagnosis as possible through the instant invention.

Furthermore, there is evidence that pelvic floor training can strengthen the pelvic floor muscles to remedy or otherwise alleviate urinary incontinence (UI) and POP, and thereby avoid surgery. Present methods for pelvic floor training, however, do not offer a way for the health care provider or the patient to measure improvement, confirm that such exercises are being performed correctly, or to accurately monitor the amount of time the patient is doing the exercises and amount of exertion the patient is using in order to improve or prevent UI or POP.

The multiple sensor-enabled device disclosed here can assist the health care provider and the patient to assess whether the patient is properly performing Kegel exercises and otherwise achieving the therapeutic goals.

Physical therapists today employ certain electronic devices to help the patient perform Kegel exercises. In these cases, a vaginal insert with sensors may be viewed as electrical impulses on a screen. But these devices cannot reflect what muscles the patient is contracting, indicate whether the patient is contracting the appropriate muscles, or monitor the patient's progress. Essentially, the only information readout is a tracing that reflects the discharge of electrical stimuli, but which offers no assurance to the health care provider or patient that the needed strengthening of the pelvic floor muscles is occurring. Electrical stimulation might provide temporary relief of UI if the electrical impulses happen to be engaged and placed correctly. However, because it is difficult, if not impossible, to know the amount of electrical discharge needed and the correct positioning, these methods do not work effectively or long-term. The electrical stimulation might allow the patient to recognize their own muscles, but falls short of facilitating the strengthening of the patient's muscles to result in an improvement, because the patient must also contract the particular muscles properly.

The multiple sensor-enabled device of the instant invention would allow the health care provider and the patient to visualize whether the patient is actually doing the pelvic floor exercises correctly. Moreover, educating the patient on the correct way of using the device would allow the patient to take the device with her, and in the privacy of her home, visualize her exercise regimen through a convenient display, such as a computer or smart phone application. The patient may also benefit from inserting, removing and cleaning the device at her convenience. Furthermore, the patient can monitor and record her progress and send her information back to the health care provider to assure her compliance. The convenience and privacy of home training and progress monitoring can enhance patient compliance with the therapeutic regimen, and facilitate a more efficient achievement of therapeutic goals.

BRIEF SUMMARY OF THE INVENTION

The present invention relates to the diagnosis and treatment of pelvic organ prolapse (POP). In an embodiment of the invention, this diagnosis and treatment involves the use of a multiple sensor-enabled device for vaginal insertion capable of providing real-time data regarding the patient's physiology, the position and movement of the urethra, and the muscular strength of the patient's vagina and pelvic floor. In one embodiment, the device may be inflatable.

The multiple sensor-enabled device may include at least one sensor capable of providing real-time data of one or more types selected from the group consisting of position, movement, pressure, and flow. In this regard, a sensor may have a single measurement and reporting capability, or may have multiple measurement and reporting capabilities.

The present invention also includes a method for the diagnosis or treatment of urinary incontinence (UI) or POP comprising providing a multiple sensor-enabled device in a patient and determining the anatomical state of the patient capable of relieving the incontinence. The device can indicate the position of the patient's urethra and vagina, and allow the health care provider or patient to visualize the relative movement of these anatomical organs, and thus, show the patient whether her efforts at performing Kegel exercises are being performed correctly.

Often, the proper performance of Kegel exercises is difficult to explain and difficult for the patient to understand how to achieve. If the patient misunderstands how to perform such exercises, she can perform them wrong, usually by performing a valsalva maneuver and consequently causing more damage to the pelvic floor by causing the abdominal contents to be pushed down through the pelvic floor.

The multiple sensor-enabled device of the present invention would also enable the health care provider and patient to view quantitatively what vaginal pressure is being exerted by the patient at any time, to recognize the vaginal muscular strength, and to facilitate the patient's performance of muscular exercises in a precise manner. The position and pressure of the posterior vaginal wall as well as that of the lower intestines and rectal area can be determined using the device.

In an embodiment of the present invention, where the device includes inflatable components as shown in FIG. 1 as an example, POP could also be alleviated or prevented by placing the device into the vagina and inflating each section from farthest to the most proximal.

The most proximal inflatable section may be inflated to prevent spillage of the vaginal contents. In this mode of operation, the device offers advantages over devices, such as pessaries, used today. Every month, rather than the patient having to return to the health care provider to extract the pessary and clean it for reinsertion, the patient would be able to withdraw the instant device and clean it for reinsertion in the convenience and privacy of her own home, which may include any location outside the health care provider's office or facility. In this regard, the device disclosed here may be used to improve a woman's vaginal muscular strength by performing vaginal strengthening exercises (VSE) to achieve her desired sexual health as well as to address any UI or POP conditions.

The present invention contemplates the real-time position and movement tracking described in International Patent Application PCT/US2010/053712, and the multiple sensor-enable device described in U.S. provisional patent application Ser. No. 61/563,889, which are hereby incorporated in their entirety by reference. In this regard, the real-time position and movement tracking may include sensing the position of the anatomical organ of interest to an anatomical reference point, such as the patient's pubic bone, the coccyx or the vagina, or to an external reference point, such as a target on a patient's garment or in the patient's surroundings. The method may be performed in real-time, for example, during a medical examination, procedure, or surgery. In another embodiment, the method may be performed at multiple time intervals. The multiple time intervals may occur, for example, pre- and post-event, wherein the event may be pregnancy or menopause.

The multiple sensor-enabled device may also provide pressure data, which reflects muscular strength, and provide a health care provider a detailed map of where the weakest anatomical points are for purposes of POP diagnosis and treatment. Where vaginal strengthening exercises are inadequate to prevent or relieve UI or POP, a surgeon would be able to use this information to target corrective procedures appropriately.

BRIEF DESCRIPTION OF THE DRAWINGS

FIG. 1 depicts a lateral view of an embodiment of the present invention including pressure sensors 10, positional sensors 20, inflatable compartments 30, and graphical user interface 40.

DETAILED DESCRIPTION OF THE INVENTION

When used in the claims, the terms "a" and "an" and "the" and similar references in the context of describing the invention (especially in the context of the following claims) are to be construed to cover both the singular and the plural, unless otherwise indicated herein or clearly contradicted by context. Also when used in the claims, the terms "comprising," "having," "including," and "containing" are to be construed as open-ended terms (i.e., meaning "including, but not limited to,") unless otherwise noted. To the extent used, the recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Variations of the embodiments may become apparent to those of ordinary skill in the art upon reading the description. Accordingly, this invention includes all modifications and equivalents of the subject matter recited in the claims appended hereto as permitted by applicable law. Moreover, any combination of the described elements in all possible variations thereof is encompassed by the invention unless otherwise indicated herein or otherwise clearly contradicted by context.

For purposes of the present invention, the term "urethra" may be defined as the canal leading from the bladder, discharging the urine externally. See STEDMAN's MEDICAL DICTIONARY, at page 2072 ($28^{th}$ ed). In females, the urethra is a canal about 4 centimeters long passing from the bladder, in close relation with the anterior wall of the vagina and having a long axis that parallels that of the vagina opening in the vestibule of the vagina posterior to the clitoris and anterior to the vaginal orifice. Id. The term "urinary bladder" refers to a musculomembranous elastic bag serving as a storage place for the urine, filled via the ureters and drained via the urethra. Id. at page 226. The term "bladder neck" is defined as the smooth muscle of the bladder neck is histologically, histochemically and pharmacologically distinct from the detrusor muscle proper and so the bladder neck should be considered as a separate functional unit. See GRAY's ANATOMY, at page 1290 ($39^{th}$ ed.). The arrangement of smooth muscle in this region is quite different in males and females, and therefore each sex is described separately. In females, the bladder neck consists of morphologically distinct smooth muscle. The large diameter fasciculi characteristic of the detrusor is replaced in the region of the bladder neck by small diameter fasciculi which extend obliquely or longitudinally into the urethral wall. Id. In the normal female the bladder neck which above the pelvic floor supported predominantly by the pubovesical ligaments, the endopelvic fascia of the pelvic floor and levator ani. These support the urethra at rest; with elevated intra-abdominal pressure the levators contract increasing urethral closure pressure to maintain continence. This anatomical arrangement commonly alters after parturition and with increasing age, such that the bladder neck lies beneath the pelvic floor, particularly when the intra-abdominal pressure rises. The mechanism described above may fail to maintain continence (incontinence as a result of urethral hypermobility).

As commonly understood, the term "vagina" refers to an elastic muscular canal that extends from the cervix to the vulva. Although there is wide anatomical variation, the length of the unaroused vagina of a woman of child-bearing age is approximately 6 to 7.5 cm (2.5 to 3 inches) across the anterior wall (front), and 9 cm (3.5 inches) long across the posterior wall (rear). The vagina connects the superficial vulva to the cervix of the deep uterus. In a typical woman standing upright, the vaginal tube points in an upward-backward direction and forms an angle of slightly more than 45 degrees with the uterus. The vaginal opening is at the caudal end of the vulva, behind the opening of the urethra. The upper one-fourth of the vagina is separated from the rectum by the recto-uterine pouch.

In the present invention, for example, a device for vaginal insertion may be equipped with at least one sensor capable of providing real-time data of one or more types selected from the group consisting of position, movement, pressure, and flow. In this regard, a sensor may have a single measurement and reporting capability, or may have multiple measurement and reporting capabilities. The data obtained by the multiple sensor-enabled device may be reported in any number of ways known in the art, including the transmission to, and visualization on, a graphical user interface wirelessly.

The device would be inserted into the vagina until the patient feels her cervix. The distal section of the device, in an inflatable embodiment, would be filled with air, gel, liquid, or other appropriate material suitable for inflation and deflation of a compartment, to fit the patient's vagina. In an embodiment with multiple inflatable sections, the rest of the compartments could be filled from distal to proximal (vaginal opening). In this way, a patient with POP not only would strengthen her vaginal muscles but could also use the device as a pessary that can be easily removed at home and would not have the complications currently associated with pessaries, such as pressure point problems and vaginal infections.

When the device is properly inserted and inflated, the health care provider or patient can visualize the device on a display screen. When the patient is asked to perform Kegel movements, the vaginal pressure or strength of the vaginal musculature will also be visualizable on the screen. The health care provider could then go through the exercises with the patient to ensure that she is performing the exercises optimally and has understood how to interpret the information and otherwise use the equipment properly.

The multiple sensor-enabled device would be invaluable as a study or rehabilitation tool for the health care provider as well as the patient who is considering a pregnancy. The health care provider may be able to provide the patient with an exercise regimen that could strengthen her vagina and urinary musculature at home before she had her baby, helping her prevent urinary incontinence in the future and strengthening her pelvic floor, before the possible damage may occur during pregnancy and delivery.

The multiple sensor-enabled device could aid various diagnoses that rely upon data concerning the position, strength and pressures of the vaginal space. By combining pressure sensors along the multiple sensor-enabled inflatable vaginal insert along with the positional sensors, objective measurements relating to vaginal pressure and positional location can be evaluated and correlated to aid in the diagnosis and treatment of UI or POP and the rehabilitation of the vaginal muscles and pelvic floor.

In yet another embodiment of the present invention, the multiple sensor-enabled device can provide data, which is transmitted and recorded in a manner to create and maintain historical patient information for medical and/or fitness purposes, such as a pelvic floor muscle strengthening exercise calendar.

Another use for a multiple sensor-enabled device would be to correct fecal incontinence, which is often another sequela of pregnancy and childbirth. For example, if a rectocele or enterocele is diagnosed, a multiple sensor-enabled device could be inserted into the rectum. With this information the health care provider would be able to properly diagnose the etiology of the fecal incontinence whether that is due to muscle weakness of the pelvic floor, a rectal sphincter deficiency, or a combination of the two. The health care provider could target the surgical repair, in real-time if preferred, to correct the fecal incontinence.

The multiple sensor-enabled device may incorporate at least one sensor capable of measuring and/or reporting data of various types including position, movement, pressure and flow. A multiple sensor-enabled device with more than one individual sensor may be arrayed as depicted in FIG. 1. However, a multiple sensor-enabled device may incorporate a single sensor capable of multiple measurement and reporting capabilities.

The position and movement data may be of the sort measured and/or reported by any number of sensor devices, including an accelerometer, gyroscope, inductive non-contact position sensor, string potentiometer, linear variable differential transformer, potentiometer, capacitive transducer, Eddy-current sensor, Hall effect sensor, optical proximity sensor, piezo-electric transducer and photodiode array. The position and movement data may also include magnetic, electromagnetic, microelectromechanical, radio frequency, ultrasound and video.

The pressure and flow data may be of the sort measured and/or reported by any number of sensor devices, including force collector types, such as piezo-resistive, capacitive, electromagnetic, piezo-electric, optical, potentiometric, or other types, such as resonant, thermal, ionization, ultrasonic, and density (mass and index of refraction). In addition, sensor technology that recognizes movement and touch may be incorporated, which includes the types such as resistive, surface acoustic wave, capacitive (surface capacitance, projected capacitance, mutual capacitance, and self-capacitance), infrared, optical imaging, dispersive signal technology, and acoustic pulse recognition.

FIG. 1 depicts a multiple sensor-enable device for vaginal insertion with inflatable compartments. The number and precise placement of an individual sensor may vary depending on the type of positional, movement, pressure or flow measurement and/or reporting system employed. An individual sensor may have a single function or be multifunction (such as positional tracking combined with pressure and flow sensing). The multiple sensor-enabled device may also embody a video observation and/or recording device as well as an illumination source to facilitate such video capture. The precise placement of the sensor(s) and video capture component(s) need not be pre-defined, and may be configured according to the requirements of the desired application.

SPECIFIC EXAMPLES

As described earlier, the devices of the present invention may embody at least one sensor capable of measuring and reporting at least one data type, including position, movement, pressure, and flow. These include, but are not limited to, magnetic, electromagnetic, microelectromechanical, radio frequency, ultrasound and video. One example of a multiple sensor-enabled device contains various microelectromechanical (MEMS) sensors: a 3-axis accelerometer, a roll/pitch gyroscope and a yaw rate gyroscope, and a pressure and flow transducer. The sensors may be mounted on a small flexible printed circuit board (PCB) and then attached to, or incorporated within, the device. The 3-axis accelerometer tracks translation of the device in three directions. The gyroscopes are utilized to account for gravitational rotation, allowing real-time movement to be tracked.

A PCB is prepared with MEMS sensors mounted thereon. Soft leads can trail the MEMS sensors to supporting components, including, for example, a data acquisition card which may be used for transforming analog signals to digital signals. The PCB is set within the wall of the device. The location of the device may be determined by the output signals of the MEMS sensors.

In an embodiment where the multiple sensor-enabled device contains inflatable compartments, the device may be inserted in the length of the vagina at which point the compartment nearest the cervix is inflated to obtain a stationary and/or comfortable fit within the vagina. Any additional inflatable compartments may be inflated together or in sequence from distal to proximal to the vaginal opening.

The patient may be asked to perform a Kegel movement, while the health care provider and/or the patient observes the display output to confirm that the patient is performing the exercise optimally. The pressure and muscular strength of the vagina as measured by the multiple sensor-enable device would be displayed to reflect the effectiveness of the therapy. The position of the urethra and bladder neck may also be displayed in real time on a graphical user interface and/or recorded.

Following the examination using the multiple sensor-enabled device, the health care provider may conclude that rehabilitation is an efficacious option for the patient. In this regard, the measurements provided by the multiple sensor-enabled device may be recorded to facilitate appropriate patient instructions on performing Kegel exercises in an optimal manner using the visual (on-screen) information provided by the device in real-time. Once engaging the proper musculature has been successfully communicated to the patient during the medical office visit, the patient may be sent home with the instructions to perform Kegel exercises five to six times daily, for example. Four to six weeks later the patient may return for another examination using the multiple sensor-enabled device to evaluate rehabilitative treatment effectiveness, which may allow the health care provider to advise the patient about the prospects for restoring complete continence with a continued rehabilitation regime and/or a surgical procedure.

Detailed embodiments of the present invention are disclosed herein; however, it is to be understood that the disclosed embodiments are merely exemplary of the invention that may be embodied in various forms. It will be appreciated that many modifications and other variations that will be appreciated by those skilled in the art are within the intended scope of this invention as claimed below without departing from the teachings, spirit and intended scope of the invention.

What is claimed is:

1. A method for treating a female patient with a pelvic floor disorder comprising the steps of:
   (a) inserting into the patient's vagina a device comprising microelectromechanical accelerometers positioned along a length of the device;
   (b) displaying on a graphical user interface a visual representation of the patient's vagina corresponding to a position of the device that is generated by the accelerometers prior to performance of a pelvic floor exercise, and recording the position that is prior to the performance;
   (c) displaying on the graphical user interface a visual representation of the patient's vagina corresponding to a position of the device that is generated by the accelerometers during the performance of the pelvic floor exercise by the patient, and recording the position that is during the performance;
   (d) repeating steps (b) and (c) one or more times; and
   (e) generating pelvic floor position information based on the recorded positions of the patient's vagina during steps (b) and (c) and using the pelvic floor position information to guide the patient via the visual representation during at least one step (c) so as to activate pelvic floor muscles that strengthen the pelvic floor or to limit activation of pelvic floor muscles that harm the pelvic floor, thereby treating the pelvic floor disorder.

2. The method of claim 1, wherein steps (b) and (c) occur in real-time and/or wherein the device transmits the positions of the patient's vagina during steps (b) and (c) wirelessly to the graphical user interface.

3. The method of claim 1, wherein the graphical user interface is a display screen of a computer or smart phone.

4. The method of claim 1, wherein steps (b) and (c) are repeated five or six times daily and/or wherein steps (b) and (c) are performed every four to six weeks.

5. The method of claim 1, wherein the device further comprises a pressure sensor.

6. The method of claim 1, wherein the device is inserted wholly within the vagina.

7. The method of claim 1, wherein the method strengthens the pelvic floor muscles of the patient.

8. The method of claim 1, wherein the pelvic floor exercise comprises a Kegel maneuver.

9. The method of claim 1, wherein the pelvic floor exercise comprises a Valsalva maneuver.

10. The method of claim 1, wherein the pelvic floor disorder is pelvic floor weakness or pelvic organ prolapse (POP) in the female patient.

* * * * *